(12) United States Patent
Sambasivan et al.

(10) Patent No.: US 11,059,040 B2
(45) Date of Patent: Jul. 13, 2021

(54) TRANSPORT OF LIQUIDS AND SOLUTE MATERIALS IN NANOCHANNELS

(71) Applicant: ATFI, Skokie, IL (US)

(72) Inventors: Sankar Sambasivan, Chicago, IL (US); Francis R Chapman, Mount Prospect, IL (US); Jeffrey W. Donelan, Highland Park, IL (US); Christopher J. Garcia, Chicago, IL (US)

(73) Assignee: APPLIED THIN FILMS, INC., Skokie, IL (US)

( * ) Notice: Subject to any disclaimer, the term of this patent is extended or adjusted under 35 U.S.C. 154(b) by 1475 days.

(21) Appl. No.: 15/024,541

(22) PCT Filed: Aug. 29, 2013

(86) PCT No.: PCT/US2013/057298
§ 371 (c)(1),
(2) Date: Mar. 24, 2016

(87) PCT Pub. No.: WO2014/036265
PCT Pub. Date: Mar. 6, 2014

(65) Prior Publication Data
US 2016/0243545 A1    Aug. 25, 2016

Related U.S. Application Data

(60) Provisional application No. 61/695,068, filed on Aug. 30, 2012.

(51) Int. Cl.
| | | |
|---|---|---|
| *B01L 3/00* | (2006.01) | |
| *C12Q 1/04* | (2006.01) | |
| *B01D 67/00* | (2006.01) | |

(52) U.S. Cl.
CPC ............ *B01L 3/50273* (2013.01); *C12Q 1/04* (2013.01); *B01D 67/0088* (2013.01); *B01D 2323/283* (2013.01); *B01D 2323/36* (2013.01); *B01L 2200/0642* (2013.01); *B01L 2300/0816* (2013.01); *B01L 2300/0896* (2013.01); *B01L 2400/0466* (2013.01); *F28F 2255/20* (2013.01); *G01N 2333/01* (2013.01)

(58) Field of Classification Search
CPC ......... B01D 67/0088; B01L 2200/0642; B01L 2300/0896; B01L 2400/0466; B01L 3/50273; F28F 2255/20
See application file for complete search history.

(56) References Cited

U.S. PATENT DOCUMENTS

| | | | |
|---|---|---|---|
| 6,652,627 | B1 | 11/2003 | Tonkovich et al. |
| 2004/0197843 | A1 | 10/2004 | Chou et al. |
| 2005/0238810 | A1* | 10/2005 | Scaringe ............... B82Y 30/00 427/249.1 |
| 2006/0127743 | A1 | 6/2006 | Lee et al. |
| 2008/0044893 | A1* | 2/2008 | Pollack ............... C07K 1/1136 435/305.3 |
| 2009/0101308 | A1 | 4/2009 | Hardesty |
| 2009/0305273 | A1 | 12/2009 | Cao et al. |
| 2010/0122899 | A1 | 5/2010 | Hartman et al. |
| 2010/0159462 | A1 | 6/2010 | Takayama et al. |
| 2012/0095443 | A1 | 4/2012 | Ferrari et al. |
| 2013/0004309 | A1* | 1/2013 | Sambasivan .......... C04B 35/522 415/208.1 |
| 2013/0195723 | A1 | 8/2013 | Ramsey et al. |

OTHER PUBLICATIONS

Helmenstine, Anne Marie; PhD. "Boiling Definition in Chemistry", <https://www.thoughtco.com/definition-of-boiling-604389>, Sep. 5, 2019. (Year: 2019).*
Mar. 3, 2015 International Preliminary Report on Patentability for PCT/US2013/057298.

* cited by examiner

*Primary Examiner* — Lyle Alexander
*Assistant Examiner* — Bryan Kilpatrick
(74) *Attorney, Agent, or Firm* — Hahn Loeser & Parks LLP

(57) ABSTRACT

Transport of a vaporizable liquid containing at least one solute through a material containing nanochannels is performed by contacting material with at least one vaporizable liquid component and inducing liquid transport along nanochannel interior wall surfaces, wherein the material contains nanochannels having an average diameter up to about 300 nm, preferably up to about 100 nm, and liquid transport is induced by partial liquid vaporization. A film of solid material is deposited onto an interior nanochannel wall surface by removing the transport liquid.

22 Claims, No Drawings

TRANSPORT OF LIQUIDS AND SOLUTE MATERIALS IN NANOCHANNELS

CROSS-REFERENCE TO RELATED APPLICATIONS

This disclosure claims the benefit of priority to PCT/US2013/057298 filed Aug. 29, 2013 which claims the benefit of priority to U.S. Provisional application No. 61/695,068 filed Aug. 30, 2012, the disclosures of which are incorporated herein in their entirety.

BACKGROUND OF THE INVENTION

This invention relates to transport of liquid through nanochannels by generation of local pressure gradients through partial vaporization of liquid within such channels, and more particularly relates to transport of liquid containing solutes through the channels and deposition of solute material or a modified form of solute material onto the interior channel wall surfaces.

Recent efforts in nanofluidics have focused extensively on enabling fluid flow within nanodimensional pipes or channels in which flow characteristics are distinct from that in larger channels or tubes due to dominating surface or wall effects. Breakdown of continuum Navier-Stokes equations has been observed in channels of about 80 μm or less, and flow properties in smaller channels become significantly less predictable by those equations. Primary modes to flow or transport liquid through nanopipes or nanochannels (e.g., having average diameters less than about 300 nm, preferably less than about 100 nm) are hydrodynamic and shear force flow (through application of an external pressure gradient), electro-osmotic (driven by application of an external electrical field or ion interactions with the pore wall), and capillary action (driven by surface tension of the liquid). These methods rely on application of an external force.

Flow through nanochannels is important in many applications, including biosensing, drug manufacture and dosing, filtration/purification/separation, power generation, cooling, and the like. While progress is being made in nanofluidics, a large and unmet need relates to ease of inducing flow in nanochannels, to control or enhance flow rates, and to enable continuous flow systems. Deposition of solids as thin films on interior wall surfaces of nanochannels also is highly desired for many applications. Solid films within nanochannels can functionalize the wall surface, such as to provide catalytic materials or barrier protection over a range of temperatures and environments; to place multiple film layers having the same or different compositions onto the interior wall surface of a nanochannel; to modify surface energy; to absorb preferentially certain species in flowing fluid; to enable smooth flow and separation of biomolecules; and to place conformal films on nanometer-sized vias in a semiconductor or electronic device surface structure in multiple layers to form nano layered functional devices such as transistors or diodes.

There is a need for new and practical methods to enable and control flow and transport of liquids and solutes through nanochannels and to place solid materials onto channel wall surfaces.

SUMMARY OF THE INVENTION

Transport of a vaporizable liquid containing at least one solute through a material containing nanochannels is performed by contacting material with at least one vaporizable liquid component and inducing liquid transport along nanochannel interior wall surfaces, wherein the material contains nanochannels having an average diameter up to about 300 nm, preferably up to about 100 nm, and liquid transport is induced by partial liquid vaporization. A film of solid material is deposited onto an interior nanochannel wall surface by removing the transport liquid.

DESCRIPTION OF THE INVENTION

In accordance with this invention, flow of a suitable transporting liquid is induced by contact of a material containing nanochannels under operating conditions of temperature and pressure that produce internal partial vaporization of the liquid within a nanochannel, which drives a liquid flow along the nanochannel walls. In an aspect of the invention such liquid flow is induced by partial vaporization of at least one vaporizable component in a transporting liquid such that gas pressure gradient drives liquid along a nanochannel interior wall. Because liquid flow is driven by gas flow, preferably, nanochannels are not filled completely with liquid, and preferably there is an open gas communication between a vaporizing liquid interface throughout the nanochannel.

An aspect of this invention is transport of a liquid through a material containing nanochannels, and particularly flow of liquid along interior nanochannel walls. In such transport, a suitable liquid contacts at least one surface of the nanochannel-containing material, and the nanochannels typically are in open communication with the surface through a network of nanochannels and microchannels. Microchannels typically are larger than nanochannels, with an average diameter greater than 300 nm, and serve as access points which enable flow of a transporting liquid into adjoining nanochannels. As provided in this invention, a suitable liquid contains at least one vaporizable liquid component that partially vaporizes at operating conditions and induces liquid transport through the nanochannels. Partial vaporization provides sufficient gas pressure to maintain a gas flow along a nanochannel in the direction of lower pressure, which flow is sufficient to drive liquid along the interior nanochannel walls. Typically, due to small dimensions within a nanochannel, a sufficient pressure gradient can be generated to induce flow with a low amount of vaporization and complete vaporization of the liquid is not desired. Preferably, the transporting liquid at least minimally wets the interior wall surface, although typically there is no need to use liquids compatible with specific surface charges or polarity or require nanochannel wall surfaces to have specific surface energy or chemistry, such as matching polar and non-polar surfaces and liquids, to induce liquid flow. Typically, induction of flow is not dependent on adhesion of the liquid to such surfaces as demonstrated by use of polar versus non-polar transporting liquids. Typically, liquid will vaporize along the entire liquid gas interface up to the dew point of the vapor, i.e., until the local nanochannel volume is saturated with the vaporized liquid. Although such a liquid may not flow on the surface of larger channels, if a larger channel is connected to nanochannels, spontaneous surface flow from liquid in the nanochannels may drive surface flow in adjacent larger channels, cavities, or pores.

Typically, liquid film thicknesses in this invention typically is at least about 10 nm, typically at least about 20 nm and preferably at least about 40 nm, and typically is less than about 150 nm, typically less than about 100 nm, and preferably may be less than 80 nm. In general, liquid film thickness is less than half the size of a given constriction to be transported through Nanoflow. At these nanoscale thicknesses, the effect of viscoelastic properties becomes increasingly negligible and van der Waals, electrostatic, and vapor pressure effects dominate flow characteristics.

In another aspect of this invention, a continuous flow of liquid is transported through the nanochannels as long as sufficient vapor pressure and liquid reservoir is present maintaining a continuous uniform thickness liquid film throughout the nanochannel or porous body. Furthermore precise transport rates of both solvent and or solute may be metered within a nanochannel in a continuous manner.

A suitable transporting liquid should be capable of a phase transition from a liquid to a gas within a nanochannel under operating conditions. A suitable transporting liquid contains at least one vaporizable liquid component that acts to drive liquid transport by induced internal liquid vaporization. A suitable transporting liquid may be a mixture of liquids and may contain one or more vaporizable liquid component. Thus, a transport liquid may contain water or water in combination with an alcohol as a vaporizable liquid component. Typically, a transporting liquid contains at least 5 wt. %, preferably at least 25 or 50 wt. %, vaporizable component. The transport liquid may be entirely a vaporizable liquid.

Preferable transporting liquids include polar and non-polar liquids including organic solvents such as $C_1$-$C_{10}$ alcohols, aldehydes, ketones, ethers, hydrocarbons, halogenated hydrocarbons, aromatics, aliphatics, and the like. Preferably, transport liquids are capable of solvating a solute material that will be placed onto the interior walls or transported through nanochannels. Water or a mixture of water with miscible organic liquids may be useful as a transporting liquid. In accordance with this invention a liquid film flow occurs spontaneously as liquid flows along walls of very narrow or small channels and may induce flow through channels of larger dimensions. If biomolecules are to be transported, a preferable transporting liquid also is pharmaceutically acceptable.

A transporting liquid also may be a molten metal or alloy or a salt, provided the molten mass is sufficiently vaporizable at the chosen operating conditions to induce Nanoflow. In such a case, a nanochannel-containing body will be infiltrated at elevated temperatures and then cooled to room temperature to deposit thin metallic or alloy films. Conversely, a liquid may be infiltrated at room temperature and used as a solid film below its freezing point (such as formation of thin films of water ice). The liquid also may be an organometallic or metalorganic compound, wherein, after liquid flow in the nanochannels, suitable thermal conditions are established to enable pyrolysis and deposition of a solid film similar to an in-situ chemical vapor deposition. Suitable solutes should be soluble in the transport liquid under conditions used and may be capable of adhering or functionalizing an interior channel wall surface.

In a preferable aspect of this invention, a transporting liquid contains a solute that is transported along the interior nanochannel walls together with the transporting liquid film. It is believed that a suitable liquid containing a solute flows on the wall surface in a nanochannel to form a film, which when dried creates a coating of a solid residue on the wall surface. After pyrolysis/decomposition or evaporation of the liquid film, a layer of solid solute remains on the nanochannel walls. Multiple layers of solid solute may be created by repeated treatments according to this invention.

After a liquid film is deposited, the film may be modified with removal of solvent and adhesion of solute on wall surface. With subsequent heat or other means to evaporate or decompose the liquid, the solute layer may be further modified (e.g., undergo a chemical transformation under the conditions used to remove liquid) and bonded to the wall surface. Upon further heating or curing under vacuum or atmospheric conditions, substantial portion of the liquid may be driven off leaving a layer of solid material or the liquid layer may be converted to a solid, such as a polymer resin conversion to condensed polymer. Because such liquid film was thin and uniform within the nanochannel, the resulting solid layer also is thin and uniform, and highly conformal to the nanochannel wall surface morphology. Thus, as used in this invention a remaining solute layer includes dried solute residue and solid products remaining after liquid removal such as by heat, which may be modified further by continued heating (e.g., pyrolysis) or other chemical or physical treatment. Such solute layers can fundamentally change surface chemistry and morphology of nanochannel walls and such surfaces can be tailored for subsequent use in sensing, catalysis, separations, enhanced flow, and the like.

Transport of liquid and liquid containing a solute according to this invention is induced by liquid vaporization within the interior of a nanochannel. Typically, such inducement is accomplished by local heating of a vaporizable liquid component to a temperature at which sufficient vapor pressure results. For an aqueous transport liquid, a typical suitable temperature typically is above about 40° C. and preferably above about 50° C., and typically is less than about 80° C. and preferably is above 70° C. A preferable temperature is about 60° C.±2° C. at normal atmospheric pressure conditions. Preferably, the vaporizable liquid such as water is not heated to a boiling temperature. A method to increase gas Nanoflow rate is to reduce the ambient pressure or reduce solvent/solute wall interaction and drag by changing polarity of wall surface chemistry.

Preferably, this invention is applicable to liquids containing solutes. In general, the liquids can be mixture of solutes and solvents so long as one component of the liquid is vaporizable under operating conditions of temperature and pressure. Another aspect of this invention is to deposit a solid film on internal surfaces of nanochannels. In this aspect, a liquid containing a solute flows along the walls of nanochannels that typically are contained in a porous body (e.g., a material containing an interconnected array of nanochannels). A solvent containing a solute, which typically and preferably is completely dissolved (i.e., is clear and contains no particles or suspended solids) with sufficient concentration to adhere to the nanochannels of the porous body after the solvent is dried or pyrolyzed. Different solutes may be favorable for different applications, for instance a solute which may deposit as a dense film may be desirable for tailoring the pore channel size/shape, providing a barrier, or altering frictional or uniformity properties. However a solute, which may deposit as a deliberately rough or irregular coating, may be desirable for applications where an increase in surface area is desired. In addition to spatial tailoring of pore structures, substantial applications are expected to be found where surface functionalization is desired, for example, in catalysis, flow diagnostics and metering, affinity chromatography, DNA separation/sensing, and engineering of chemical potential. Without limitation, such functionalizations can include hydrophobic, hydrophilic, oleophobic, ligand exchange, and ion exchange. More specifically, a cationic or anionic functionality can be deposited to meter flow through the nanochannel via solute charge or externally applied electrical field. In another aspect of this invention electronic, magnetic, or dielectric films or stacks may be manufactured for various applications relating to batteries, fuel cells, semiconductor devices, solid state phosphor lighting, piezoelectric materials, information storage mechanisms, thermal and environmental barriers, separation, chromatography, and the like. In another aspect of the invention a metal, metal oxide, or spinel oxide precursor solution can be deposited on pore walls and pyrolyzed to an appropriate temperature to create a pure metal or metal oxide on the pore wall surfaces creating high surface area conductors. Multiple layers of solid film may be deposited onto the interior surface of a nanochannel, each layer having the same or different compositions. Typically, the number of layers is fewer than needed to fill the nanochannels.

A solute may be a metalorganic compound, or mixtures of metal organic compounds, soluble in a polar solvent (e.g., platinum or aluminum acetylacetonate, indium acetylacetonate, or tin acetylacetonate in acetylacetone or a ketone) or an organometallic compound soluble in a nonpolar solvent. A metal-containing solute exhibiting electromagnetic (flow control of liquids by externally applied electric or magnetic field) or piezoelectric properties may be used. Another possible solute may be an organic semiconductor or organic electromagnetic compound. Suitable solutes may include a precious (e.g., gold, platinum, palladium, iridium, silver, rhodium), or a conductive metal chelated to an organic group; combinations of more than one metal component attached to an organic or a metalorganic or an organometallic component; a material that converts to a transition metal oxide or a mixture of transitional metal oxides; a material such as silver having antimicrobial properties; a material capable of attachment to a biomolecule such as an antibody. Another possible solute may be a medium or high yield polymer resin with appropriate content and nature of solvent, which converts to a solid polymer layer upon gentle heating.

In an aspect of this invention, multiple solutes may be transported within a nanochannel at different rates. This permits separation of solutes based on such rate differential. Because two-phase liquid film thicknesses approach the thickness of tens to hundreds of molecules, wall solvent and solute interactions are a primary force in flow. Furthermore, the nanochannel size, configuration, density, and surface chemistry may be altered to improve or hinder flow of certain molecules. Solvents and solutes with different polarity and charge will experience different drag coefficients when continuously flowing through a nanochannel array. Specifically, a polar or non-polar surface chemistry may be desirable to increase or decrease liquid transport rates. Rate of separation may be controlled by altering solvent vapor pressure, external temperature, separation path length, or concentration. In another aspect. a specific binding agent may be deposited to allow for specific bonding of a particular functional group. In the case of biomolecules, an antibody, enzyme, or noble metal may be deposited to prevent or decrease the flow of a specific chirality or protein sequence. Molecules may be extracted from the surface by an eluent or external force such as pressure, temperature, or the like. In a further aspect of this invention solvent may be dried to form a solid film on the wall and the nanochannel or porous body may be sections at which point the solute can be re-solvated as a fraction of the separation.

In one aspect of this invention, a film is deposited on pore (nanochannel) walls of a porous body or a nanopipe by flowing a liquid film on the pore wall and subsequently drying the liquid under ambient or thermal conditions in order to drive off the solvent as vapor to leave a solute residue behind on the pore wall. Without wishing to be bound by theory, liquid film is spontaneously formed on internal pore surfaces and the film spreads through a substantial portion of the porous body by solution film flow on nanochannel walls, in a thin and conformal manner, preferably where there exists a gap between parallel pore walls. This phenomenon may be called Annular Flow, Two-Phase Boundary Flow, or Nanoflow. Nanoflow is theorized to be a mechanism wherein evaporation of the transporting solvent generates zones of increased local vapor pressure, resulting in pressure gradients at a film front, which make forward flow favorable. The flow rates are enhanced in nanochannels due to a cooperative movement arising from a two-phase flow of gas at the core of the nanochannel alongside the liquid film on the annular region. Flow conditions are sustained as long as a locally dynamic vapor pressure gradient (i.e., within the region of liquid flow) remains in, or favoring, the direction of the flow. Local pressure (and hence the rate of the flow) typically is dictated by the evaporated molecules in the cavity within the wall film. Flow of liquid film generates additional surface area for inducing evaporation and the cycle continues until the solution approaches a dead end, constriction, opposing film front, or an exterior surface. Flow rates may vary depending on local cavity or domain size. For example, when liquid approaches a relatively large cavity, the flow rate is reduced. However, if the large cavity reconnects with a small nanochannel, the flow rate is enhanced again. Thus, the amount of local pressure created dictates the flow rate. The flow rate may also be enhanced by external factors, such as pressure or vacuum or temperature.

Without being bound by a specific theory, initial movement of liquid into a material containing nanochannels appears to flow substantially on interior surfaces of such nanochannels. Such flow appears to be controlled by thermodynamic means, such as a partial vapor pressure (fugacity) or chemical potential gradient of the vapor species in the direction of liquid flow. Flow may be initiated by converting a relatively small portion of the liquid into vapor molecules within the nanochannels, which establishes a pressure. Subsequently, a flow condition is achieved whereby the flow rate of the liquid film is dictated by local pressure generated from partial vaporization or evaporation of the liquid. This type of flow may not be driven primarily by traditional capillary action. Further, in a process (i.e., liquid penetrating into interior portions of a contacting material) according to this aspect of the invention, liquid that may contain dissolved materials (i.e., solutes) such as salts, biomolecules, and other substances forms a thin liquid or wet film covering the interior of the nanochannels. This film appears to be substantially uniform in thickness throughout the nanochannel structure. Thus, a substantial portion of the open interior surface area in a solid body or inner surfaces of a nanotube or a nanopipe (i.e., nanochannel) is covered by a thin liquid film. As the liquid film continues to flow through the nanochannels, solute material preferentially adheres to wall surfaces and can affect liquid film flow rate. The inducement of liquid flow, and the flow rate, of the liquid depends on factors including solvent and solute charge (polar or non-polar), solute content and molecular size, wall surface energy, pressure differential (including vacuum), and nanochannel characteristic diameter, and temperature. Of these, temperature and nanochannel diameter are dominant factors in controlling pressure gradients and liquid film transport rates. If a surface contacting the liquid contains a multitude of nanochannels (or larger channels leading to nanochannels), flow can be induced in all the nanochannels at the same time. Thus, high throughput transport mechanisms can be established.

From a liquid surface, the rate of vapor molecules that escape to the gas phase is the vapor pressure of the liquid. A liquid will vaporize so long as the pressure above the liquid created by the vapor molecules is less than that of the rate of the vapor molecules escaping the liquid surface. In an open container, this process will be thermodynamically favored until the liquid is gone, i.e. completely evaporated.

When confined in a closed channel, tube, or pipe, the number of molecules that will vaporize is limited by the dew point of the vapor, and evaporation will continue only until the vapor is saturated; beyond this point the pressure of the gas phase will hinder further evaporation. If the vapor is given a space to expand into, such as along the length of an enclosed tube, then the saturation point will not be reached and continued evaporation can occur.

In an enclosed tube, the number of molecules of vapor required to generate a significant pressure that will allow gas expansion into adjacent areas is directly dependent on the tube volume. For tubes with increasingly small diameters, the number of vapor molecules required to generate such a pressure decreases in a non-linear fashion. At a tube diameter around 300 nm only about 2500 vapor molecules are required to generate a local pressure of 40 torr. Below this diameter, even fewer molecules are needed to generate 40 torr of pressure; at 100 nm diameter, around 200 molecules are need, and at 50 nm diameter, less than 60 molecules are needed. Conversely, above 300 nm, the number of vapor molecules required to generate significant local pressure increases significantly. Accordingly, under similar operating conditions of temperature and pressure, higher local pressure is generated in smaller-sized nanochannels. Higher local pressure can yield higher flow rates of the liquid film along the nanochannels.

The importance of the number of vapor molecules required to generate a local pressure is due to the limited liquid film thickness that serves as the source of vaporization. If a large number of vapor molecules are required to generate pressure, there will not be enough liquid molecules available to become vapor, and a local pressure will not be created sufficient to induce flow.

A further aspect of this invention includes infiltrating catalytic materials such as one or more catalytic metals or catalytic metal compounds onto an interior surface of a porous substrate. In this aspect, one or more thin layers of a material that is dissolvable into a suitable liquid may be applied to an interior nanochannel of a porous substrate. Such material may be a salt and may be a salt of a catalytic metal, such as a metal in Groups 3-12 (IUPAC nomenclature).

Another aspect of this invention is to fabricate nanopipes or nanostructures of any solid material by deposition of films along the walls of a sacrificial template such as a carbon fullerene, graphene stack, carbon nanotube, multi-walled carbon nanotubes, or other suitable nanostructures. Novel nanopipes of materials such as metal oxide or more specifically spinel oxides could be fabricated. Such advances are of interest as enhanced flow rates have been reported in nanopipes due to frictionless internal surfaces of carbon nanotubes. Additionally, solid nanopipes may be manufactured around a solid nanowire substrate by confining the surface of the nanowire with a "roof" which may be composed of a nanotube.

Typically the template or "roof" will be sacrificial and may be removed by annealing, etching, or other mechanisms, however in some cases the template also may serve a structural or otherwise desirable purpose. Nanofabrication methods are of great interest for applications where exposed, regular, high surface area arrays are desired, for instance for photovoltaics, hydrogen storage, fuel cells, catalysis, drug dosing and the like. Additionally, reliable fabrication of structures on the nanoscale is desired to exploit properties arising from 2D, 1D, or 0D quantum confinement, especially for electronic devices and fundamental physical studies.

Another aspect of this invention is directed to enabling thin film electronic nanofluidic devices such as diodes, capacitors, resistors, and transistors in which insulating, dielectric, semiconducting, or conducting layers are placed on the nanochannel walls. In this aspect, layers of conductive, semi-conductive, and insulating materials (as known in the art) may be applied on the interior wall surfaces of nanochannels to create a suitable electronic device.

High sensitivity biosensors may be constructed by incorporating a bioactive layer within an alternating high-k/low-k film stack on optically transparent substrates (photonic crystal). If the low-k area is left as air, this creates a nanofluidic channel, which may be functionalized with whatever biosensitive ligands are desired for the specific sensing application. Nanochannel structures may be designed such that spectroscopic signals are enhanced enough that trace biological molecules (such as proteins, DNA) may be registered or identified. This could be useful for advanced diagnosis methods for diseases. Structures that take advantage of the surface to volume ratio of nanochannels to accommodate the low concentration of the analyte such as plasmonic schemes and Fabry-Perot cavities may be improved by an ability to functionalize the channels. Functionalized nanofluidic structures have the potential to sense tens of molecules or even single molecules.

Nanofluidic electronic devices may be designed, which are biocompatible and controlled by pH or other bio-friendly means. Control of the shape of the nanochannels is important for the efficiency and configuration of nanofluidic electrical devices. Flow through a nanochannel may be controlled by depositing electrodes along the walls of the channel and applying electrical fields/currents, which may be used in flow metering.

Tailoring channel and pore sizes to preferentially admit different molecules by their size may be used to separate and sort molecules such as proteins or other biological molecules stochastically on a large scale or even one by one if so desired to achieve perfect purity. Functionalized channel-based structural networks produced in accordance with this invention may be used in desalinization and water/wastewater purification.

Nanofluidic channels may be made into pH-controlled or solute gradient controlled devices for use in power generation power in areas such as salt marshes or estuaries. Channels may be functionalized with ligands that promote travel of either positive or negative ions down the channel, thereby forming an electrochemical structure.

A solid film placed in a small channel may facilitate faster flow of a coolant in a semiconductor device and may be manufactured with appropriate dimensions for integration in such a device by such methods as altering polarity or surface charge of nanochannel walls through the deposition of a specific coating or film.

Liquid film on an interior surface of a nanochannel can serve important purposes such as performing solute analysis that may be useful in lab-on-a-chip applications with biomolecules acting as the solute in a suitable solvent.

Surface area of a catalytic surface may be increased by depositing rough or even porous films (such as porous alumina films derived from aluminum nitrate salt dissolved in alcohol with subsequent heating) along the nanochannel walls, thus maximizing the surface area available for reaction. Hydrogen storage may be enhanced by such porous layers on nanochannel walls. If the desired process reactants are gaseous or low viscosity liquids, the channel may be filled with several intentionally irregular and non-hermetic layers for substantial surface area increases. Similarly, a film deposited on channel wall surfaces through this invention, which is intentionally rough, may be used in applications where energy density is important, such as hydrogen storage and solid-oxide fuel cells.

A nanochannel treated with a solute in a non-polar solvent and subsequently treated with a solute in a polar solvent may deposit two solid materials that can be processed after solvent removal to form a compound layer for surface functional properties with or without reacting with the nanochannel wall of a substrate material.

An aspect of this invention is directed to an in situ Chemical Vapor Deposition (CVD) process in which CVD precursor layers are deposited in a nanochannel by a) dissolution of a precursor in a solvent (e.g., tin acetylacetonate in acetylacetone), b) formation of a liquid film of the solution on nanochannel wall, c) removal of the solvent upon mild heating or drying and subsequent heating of the residue to predetermined set temperatures. This results in sublimation that generates vapors of solute that react with the substrate at the internal nanochannel wall surface leading to pyrolysis of the solute precursor to deposit a film locally within a nanochannel while venting the byproducts as vapor (e.g., alumina or metal oxide, conductive oxides, silicon carbide, metal, metal nitrides, metal carbides, complex metal oxides or sulfides, gallium nitride, gallium arsenide).

An aspect of the invention is to perform deposition while flowing inert or other gases, which may be used during in situ CVD to control deposition characteristics. The in situ CVD approach may be used to deposit multilayer stack consisting of low K and high K dielectrics, metal layers (electrodes), metal compound (active or functional layer, such as a semiconductor or photovoltaic), and a top electrode layer—such as a photovoltaic cell or a semiconductor device stack or a biosensing or a gas sensing device. With respect to in situ CVD, a precursor organometallic or metalorganic compound present in nanochannels after deposition may be heated to form a vapor that favorably reacts with the wall surface to deposit a metal, inorganic or compound film. In such a deposition, the precursor compound can be dissolved in a suitable solvent and conditions for Nanoflow established. Once the solvent is driven off, the material can be heated to deposit solid films from decomposition of the precursor compound.

Using the in situ CVD approach, carbon nanotube or any conductive nanotube or nanopipes may be used as the substrate back electrode, followed by subsequent deposition of a functional metal or organic semiconductor layer(s), and optionally an additional top electrode. A multilayer stack of an electromagnetic device may be deposited using the in situ CVD method, such as to form a nanolayered composite consisting of individual functional layers.

Another aspect of the invention is to deposit conformal films on a surface of a semiconducting, electromagnetic, or electronic device, such as an etched silicon surface. A temporary cover or "roof" (such as a graphene stack) may be deposited on such etched, grooved surface structures, which may be high aspect ratio channels, vias, or other features, to form an enclosed nanochannel or nanopipe that will serve to contain vapor within a sufficiently isolated space to enable high enough local vapor pressure gradients to promote film flow along confined walls within high aspect ratio channels, vias, or other features. Deposition of a magnetic, insulating/encapsulating, dielectric, semiconducting, bioactive or conductive film may be facilitated by this aspect of the invention. Typically, the deposited film will be subsequently dried and pyrolyzed to leave behind solid residue, which in this case may be desirable to be uniformly porous or dense. Such covered etched surfaces used to form nanochannels are considered materials containing nanochannels for the purpose of this invention. Deposition of a dielectric film of an inorganic oxide or a conductive film can be done through such a method with subsequent drying and thermal pyrolysis treatment.

As used in this invention, a suitable nanochannel or "pipe" has a typical average cross-sectional diameter of up to about 300 nm, preferably up to about 100 nm, although possible channel diameters may be larger or smaller. Channels may be interconnected to form networks of channels with connected cavities or pores. Channels may be a part of a porous material containing interconnected pores and channels or may be formed in spaces between fine fibers or rods in a bundle, which are consolidated into a solid part, such as a foam. Materials of construction of such foams comprising of fine hollow or solid fibers can be metal, ceramic, polymer or carbon. A suitable channel is sufficiently narrow and confined to permit wall surface flow of a liquid along the channel under suitable conditions. Nanochannels defined in this invention do not need to be completely free of defects or holes in the nanochannels that have open communication with the exterior part of the nanochannel. Nanoflow in such nanochannels will occur so long as the pressure differential induced by vaporization can be present. Without wishing to be bound by theory, it is postulated that the rate of vapor loss from such defects or holes is relatively small compared to rate of vaporization induced by the flowing gas in the nanochannel.

Materials containing channels useful in this invention refer to interconnected channels, which typically form a complex web of internal spaces or voids of varying dimensions and form. Typical forms of channels are extended tubes, vias, and spaces of varying dimension and cross-sectional shape connected in a network. Furthermore, the nanochannel network may be modified or engineered in specific sizes or gradients to improve deposition of specific molecules or films in desired portions of the network. A porous material with open pores contains channels with open communication with the surface of the material. The terms "pores", "channels", or "pore channels" may not necessarily be descriptive of the actual shape of the internal structure of a porous material, but are used to describe the network of internal spaces contained in such materials and collectively described as pores. Although main channels may be 2 to 0.1 micrometers (2000 to 100 nanometers) in mean diameter, there may be very fine pore nanochannels connected to such main channels that have mean diameter dimensions of less than 100, typically less than 50 or less than 20 nanometers. Some pores may be macroscopic-scale voids in a material characterized by an internal surface area interfacing with a gaseous environment.

Suitable materials in which a nanochannel or network of nanochannels are formed include organic or inorganic materials that have sufficient structural integrity to maintain a dimensionally stable nanochannel. A typical suitable material should be sufficiently stable to undergo treatments used in this invention including liquid contact and heating. Materials useful in this invention typically contain interior nanochannels that have communication to the surface of the bulk material. Such channels may be interconnected and may contain additional nanochannel structures, all of which form a part of the material. Typical nanochannels useful in this invention are up to about 300 nm in average diameter and preferably up to about 100 nm in average diameter. Also, useful nanochannels typically are sufficiently constrained as to provide a volume in which increased gas pressure may be maintained. Typically, a nanochannel useful for this invention is sufficiently long to permit gas flow as described in this invention. Typical aspect ratios for such nanochannels at least 5:1, more typically more than 10:1 and may be more than 100:1. Typical path lengths for nanochannels useful in this invention are at least 50 micrometers, at least 100 micrometers, at least 250 micrometers, and may be at least 500 micrometers. A bulk material useful in this invention typically is sufficiently thick not to be considered a membrane. A typical thickness is at least 50 micrometers and preferably is at least 100 micrometers or at least 250 micrometers. Many such materials are more than 1 mm or 1 cm thick and may be thicker.

The interior nanochannels may have varying widths or sizes and typically may range from 300 nanometers (nm) or more to 30 nanometers or less. These pores typically have an irregular cross-section with diameters measured as mean (average) diameters. More typically, materials useful in this invention contain an open pore network (i.e., with open communication with the surface) with nanochannels with diameters of up to 200 nm or up to 100 nm. Some pore channels may have diameters greater than 2 nm (typically greater than 4 nm) and may have diameters of 30 nm or less, and may be up to 50 nm. Typical pore networks have channels ranging from 20 nm to 200 nm with a majority of the total channel volume within channels having diameters of 30 to 100 nm.

A typical suitable material useful in this invention contains an open pore network with combination of nanochannels and macropores having average pore diameters larger than 100 nm, but any quantity of nanochannels should be sufficient to provide a surface to enable Nanoflow. The material also may contain larger channels and pores in which typically the Nanoflow described in this invention will not occur. A preferable material containing nanochannels is a man-made article, which has been engineered, designed, or fabricated, and not a natural product. A more preferable substrate type is a sintered material, such as sintered powders, metals, ceramics, or polymers, in which a web of interconnected necking creates sufficient nanochannels to provide continuous flow. Another preferable substrate is a thermally sprayed or PVD coating containing interconnected webs of nanochannels between splat boundaries. Typical suitable materials for this invention include silica structures such as slip cast fused silica, ceramic coatings, and carbon structures such as graphite and carbon nanotubes. A preferably material containing nanochannels useful in this invention contains at least 25 wt. % carbon and silicon. Advanced Materials containing some amount of open porosity can benefit from Nanoflow-based solute deposition. Such Advanced Materials typically are used in high temperature applications, preferably above 1500° C. and more preferably above 1000 C and most preferably above 500° C. and such Advanced Materials include silicon-containing engineered ceramics, ceramic coatings, high temperature power electronics, advanced alloy metallic foams, and metallurgical coatings.

Pore volume or porosity may be measured by the Archimedes displacement method. Pore volume and surface area may be measured using the Brunauer-Emmett-Teller (BET) technique or mercury intrusion porosimetry (MIP) or other suitable techniques such as helium pycnometry.

In one aspect of this invention, a substantial degree of initial porosity of internally coated substrates is maintained. Many substrates useful as high performance materials have open-cell porosity, which can be measured as average pore volume. Because such porosity is important to the usefulness of such high performance materials (such as heat barriers), a coating that functions to protect the substrate against oxidative, moisture, water vapor, or corrosive gas degradation should not significantly affect the porous character of the substrate. Typically, there is less than 25% or less than 10% (preferably less than 2% and may be below 1%) change in pore volume after application of a coating of this invention. Thus, typically, 75% (on a volumetric basis), 90%, or more of measured initial (pre-coating) porosity is retained based on an uncoated substrate. Preferably, at least 95% of the porosity is retained and porosity retention may be at least 98% or at least 99%. Thus, a superior internal coating is thin (typically less than 2 micrometers, preferably less than 1 micrometers, more preferably less than 0.5 micrometer, more preferably less than 0.150 micrometer, and most preferably under 0.050 micrometer) and is able to coat surfaces within pores of a substrate and protect all surfaces of a porous material against oxidative degradation at extreme operating conditions experienced by such substrate including temperature and moisture and contaminant concentrations.

An aspect of this invention is coating of interior surfaces of an open porous material such that environmental contaminants cannot penetrate through size constrictions in open channels preserving and closing interior porosity. However, reduction, but not complete closing of pores may control of the smallest pore constriction or average pore constriction, and thus may be useful filtration or separation applications.

Typically, the nanochannels are in open communication with a space that permits gas flow from a pressure formed by vaporized liquid in the nanochannel to a volume of lower pressure, such as an exterior surface of the material or a larger pore. In this invention, preferably liquid is transported through nanochannels through Nanoflow. In the case of sufficiently long nanochannels (e.g., aspect ratio of 100 to 1 (length versus average diameter) that are closed at one end and open at the other hand. Such nanochannels may be characterized as blind pores. According to one aspect of the invention, liquid flow induced at the open end of a long nanochannel will be arrested before reaching the closed end due to pressure equilibration from the vaporized liquid near the closed end. Thus, Nanoflow of liquids can occur in nanochannels without open communication to the exterior or other interconnected network channels, but such flow may be arrested prior to reaching the closed end of the blind pore. Typically, liquid is allowed to flow into pore openings of a porous material by maintaining a continuous liquid contact of the surface of the porous material such that liquid precursor migrates into the pore system to form an interior liquid film onto the surface of the interior pores and channels. In this method a porous material may be immersed or bathed in liquid precursor such that some or all of the pore openings on the surface remain covered by liquid precursor for a time sufficient for such migration. In another method, liquid precursor is sprayed continuously or semi-continuously onto a surface of a porous material such that some or all of the pore openings on the surface remain covered by liquid precursor for a time sufficient for liquid migration into the pore structure. Also, continuous contact of liquid to a porous surface may be performed by maintaining such contact with a saturated cloth, sponge, or similar material for a sufficient time for liquid migration into the pore structure. Typically, immersion or continuous contact of at least one surface with liquid of about 1 minute, typically at least 10-15 minutes, and may be at least 20 minutes or longer as needed to permit such migration. Such continuous contact is distinct from mere brushing, flowing, dipping, or spraying of a liquid onto a surface in which there is insufficient time to permit liquid migration into the interior pore structure.

In a typical procedure, a substrate containing nanochannels or a network of nanochannels (typically in conjunction with micrometer-scale channels and pores) is contacted with a transporting liquid solution with a desired solute. After the solution is permitted to flow into the nanochannels in accordance with this invention, the interior wall surfaces of the substrate are covered with a thin film of liquid. Subsequent treatment, typically with elevated temperatures or reduced pressure, causes evaporation of the liquid and leaves a film of solids on the interior channel walls. The temperature required may differ depending on the vapor pressure of the liquid and may range from 0 to 200° C. or more, typically 20 to 150° C., which may be adjusted according to the external pressure. The solid film subsequently may be heated further or pyrolyzed to effectuate a transformation of the film into another form depending on the heat stability of the underlying substrate. Temperature is the preferable parameter to control flow rates, and such thermal input can be provided either locally, for example by enveloping the nanochannel area within a device or component through the use of heat tape wrap or designed resistive heater circuit. In addition, a thermal gradient can be set within the domain of nanochannels to control flow rates in certain nanochannels.

A material or substrate that contains nanochannels suitable for use in this invention also may include an interconnected network of larger channels or pores (i.e. channels or pores >100 nm). As believed in this invention, nanochannels will undergo an annular flow mechanism to distribute a liquid film onto the interior surface of the nanochannels and further may facilitate liquid flow along wall of interconnected larger pores or channels. Such larger pores or channels typically may range up to about 1 micrometer in characteristic diameter, although there may be some effect in larger pores and channels. Typical substrates containing a network of nanochannels in combination with larger channels and pores useful in this invention contain more than 1% by interior open surface area of nanochannels, preferably at least 10%, typically more than 20%, 30%, 50%, 75%, 90% or more. In presence of suspended solids, liquid appears to engage in flow within nanochannels by filtering the larger particles out of solution during transport through microchannels or capillary network. The filtration efficiency depends on size of the particle and relative size range of the material containing the nanochannels. A device containing a combination of micro and nanochannels can be designed such that the microchannels are on the exterior portion of the device serving as a filter for most of the suspended solids and as the liquid subsequently enters the nanochannels placed on the interior of the device, it will serve as the final filter for finest solid particles. The size of microchannels or capillary network adjacent to nanochannels that serve as access points for inducing Nanoflow.

A transport liquid suitable for use in this invention should have a viscosity sufficiently low to permit flow at operating conditions of temperature and pressure. A suitable transport liquid typically is a sufficiently volatile liquid solvent at operating temperatures to permit in-channel volatilization during the method of this invention.

A preferable interior layer (which may have more than one sublayer) of solid within a porous material in this invention conforms to the interior surfaces of the material. Typically, repetitive applications of a transporting liquid into a nanochannel-containing substrate followed by liquid evaporation and typical heat transformation will produce multiple sublayers of solids on interior channel walls. Each sublayer may be about 1 to 50 nm thick, such that as layers are built up, small mesopores (e.g. 30 nm or less in average diameter) channels may be completely filled may be blocked at narrow channel constrictions. However, the remaining coated channels have a pore volume sufficient to maintain beneficial properties of the porous material. Furthermore, the material containing nanochannels generally remains substantially unchanged in density and degree of open communication of the internal channel network. Depending on the application an internal coating layer of this invention typically is at least about 1 nm and may be up to 150 nm, preferably up to 50 nm, and typically up to 30 nm thick. A typical thickness range for an internal coating layer (including sublayers) is 1 to 150 nm.

Although multiple sublayers may be used, application of many multiple sublayers will fill the open pore and channel system, which may affect some physical or mechanical properties of the material; however, typically the total weight gain from coating application within the pores is less than 10 wt. % and typically is less than 5 wt. % and may be less than 2 wt. %.

Coverage of internal structures of porous materials with solid residues or films as described in this invention typically may be observed using scanning electron microscopy (SEM) or transmission electron microscopy (TEM) with representative samples of such materials.

An aspect of this invention is a porous substrate in which macropores are internally coated, and mesopores are substantially (e.g. >50%) filled or blocked, with solid residues or films as described in this invention. In some aspects, constrictions within the pore and channel system in the porous substrate are blocked, which transforms an open pore system into a partially closed pore system. Because much of the pore structure remains, the density of the porous substrate may not change significantly (<10%, typically <5%, preferably <1%) after application of internal coating. This may be observed by measuring weight gain (or density) of a porous substrate after internal coating in accordance with this invention.

An embodiment of this invention is a device for filtration of liquids. A preferable example of this embodiment is a water filter. A water filter may be formed as a porous solid body enclosed in a container for confinement of the fluid to the interior of the solid body. The porous body contains an internal network of nanoscale pores and channels that are in open communication with the exterior of the body such that a plurality of indirect/tortuous pathways exist from one side of the body to the other side. The container enclosing the solid body is made to fit with a gas tight seal, with a single inlet opening and single outlet opening on opposite sides of the body, such that a fluid must pass directly through the interior of the solid body. The inlet opening allows fluid to be introduced directly into the interior of the solid body, preferably through the use of a feed line that is inserted directly into the interior of the solid body, such as is done with a feed-through type connector. Similarly, the outlet opening allows collection of fluid that has passed through the solid body and may include a condensing apparatus to assist in fluid collection. Finally, the enclosed porous body has a heat source, such as a small electric heating or cooling jacket element, which surrounds the enclosed porous body and allows the application of heat to controllably change the temperature and flow rate. The filter functions through using the Nanoflow method. The liquid to be filtered is put into contact with the interior of the porous body through the inlet. Heat is applied to the device to bring the temperature up to the point where the vapor pressure of the solvating fluid(s) is significant, inducing Nanoflow. Liquid flow is thus enabled to the other side of the device (outlet). The degree of filtration achieved depends on the size of the solute molecules or particles to be removed from the liquid relative to the size of the smallest constrictions within the porous body, as well as interactions between the walls of the pores and channels within the porous body and the solute molecules or particles. The rate of filtration depends on the Nanoflow conditions, including solvent, temperature and porous body constriction size.

Another embodiment of this invention is a device for precise dosage or delivery of biomolecules or pharmaceuticals. A semiconducting device, silicon wafer, polymer, or pharmaceutically acceptable substrate with precisely etched, drilled, or fabricated vias is covered with a "roof" to enclose nanochannels with a known volume, geometry or calibrated flow rate. The substrate containing nanochannels is placed in contact with a liquid containing a pharmaceutical or biomolecule. The solution then is permitted to flow into the nanochannels through spontaneous Nanoflow or Nanoflow induced by external heat or pressure. The fluid is allowed to evaporate fully depositing a solute on the pore walls where a known or calibrated volume of biomolecules or pharmaceuticals deposited on the pore walls. The device can be stored until the device later is contacted with a vaporizable liquid, and the solute is delivered at a precise rate or volume. In a further aspect, the temperature of the device is lowered to a point at which vaporization of the liquid is insufficient to induce flow. The device then can be heated until the vapor pressure of the liquid is sufficient to induce flow. Furthermore, slight variations in temperatures will allow for precise control of flow rate and volume.

This invention is illustrated, but not limited, by the following examples.

Example 1

A sample of slip cast fused silica (SCFS) was measured by mercury porosimetry to have the following properties:

| | |
|---|---|
| Median pore diameter (volume) | 0.1591 μm |
| Median Pore Diameter (area) | 0.0677 μm |
| Average Pore Diameter (4V/A) | 0.0833 μm |
| Smallest Pore Diameter | 0.0043 μm |
| Bulk Density | 1.9321 g/mL |
| Apparent (skeletal) Density | 2.1812 g/mL |
| Porosity | 11.3965% |

Three samples of SCFS were machined into 20×9×9 mm pieces. One piece was sealed on four sides with Crystalbond™ 509 (SPI Supplies/Structure Probe, Inc., West Chester, Pa.) so that two parallel 9×9 mm unsealed surfaces remained. This sample represents an infinite path length for vapor travel but requires the vapor to flow though a tortuous path of nanochannels for the entire 30 mm length of the piece. Another piece was sealed on five sides with Crystalbond™ 509 such that one 9×9 mm surface remained unsealed. This sample represents a finite path length for the vapor to travel through a tortuous path of nanochannels. The remaining sample was not sealed on any side and represents an infinite path length for vapor to travel with significant surface area on the exterior surface allowing for a significant volume of vapor paths. The three pieces were placed in a dish such that an unsealed side was placed in the base of the dish with the 25 mm dimension perpendicular to the surface of the liquid. Approximately 2 mm of a solution containing approximately 0.1 mg/mL methylene blue (Alpha Aesar, Ward Hill, Mass.) in ethanol was added to the base of the dish such that the base of the SCFS was in contact with the solution. After 16 hours the unsealed sample showed blue dye had covered the entire 20 mm of the height on the exterior of the sample but the top surface contained no dye. The sample was cut in half parallel to the long dimension and the flow pattern was observed and measured. A uniform parabolic arch-like penetration of the dye was observed from both edges of the surface with a central portion penetrating 4 mm and 20 mm in length at the base. An average rate of flow was calculated from the side surface towards the center to be 10.2 μm/min where a faster rate is observed in the initial flow regime. This rate did not account for the tortuous path through the nanochannels that the liquid film and solute travels. The four and five sided sealed samples remained in contact with solution for 36.7 hours. The samples were cut in half parallel to the long dimension and the flow pattern was observed and measured. Both samples showed level penetration of the dye that was parallel to the solution surface layer. The four side and five side sealed samples showed a dye penetration of 4 mm and 10 mm and Nanoflow rates of 1.8 μm/min and 4.5 μm/min, respectively. The sealed samples confined the vapor pathway within the nanochannels, thus creating a pressure differential sufficient to induce Nanoflow. The path of flow throughout the SCFS primarily was flow through a network of interconnected nanochannels. The flow path of the unsealed sample was dominated by capillary flow along the outer surface of the bulk SCFS due to the significant free open surface area and capillary forces. Thus, by altering the vapor path length it is possible to control the flow characteristics of the liquid through a material containing a nanochannel path.

Example 2

Two samples of SCFS were machined into 30×9×9 mm pieces. One piece was placed in a dish similar to Example 1, except the solution was methylene blue and water (approximately 0.1 mg/mL). The other piece was placed in a dish containing the same solution in an oven at 60° C. After 1.5 hours the pieces were removed from the solutions. The blue dye had penetrated 1 to 2 mm and 15.4 mm of the height on the exterior of the SCFS piece for the ambient and oven samples respectively. The SCFS pieces were cut in half parallel to the long dimension and the flow pattern was observed and measured. Essentially, no penetration of the dye was noted for the ambient sample. For the sample heated at 60° C., a uniform parabolic penetration of the dye was observed, similarly to the unsealed sample in Example 1, with penetration from the edge of 2.8 mm and a base length of 15.4 mm. The average rate of flow was calculated from a side surface towards the center to be 89 μm/min. By increasing temperature and vapor pressure, Nanoflow was enabled in otherwise non-usable solvent systems.

Example 3

A solution was made by mixing 4 mL of a yellow iodine tincture USP solution containing 2% iodine in water (Walgreens Co, Deerfield, Ill.) with 5 mg of methylene blue in 50 mL of ethanol resulting in a green colored solution. A solution of the same proportions was also made in methanol resulting in a similar color to the previous solution. Three pieces of SCFS were machined and sealed on four sides similar to Example 1 except paraffin wax was used for sealing. One piece of was placed in the ethanol mixture while the two remaining pieces were place in the methanol mixture. One of the methanol mixture samples was brought into contact with the solution at ambient while the other sample was placed in a freezer at −6° C. After approximately 30 minutes, all three pieces showed separation of color with a yellow/brown penetration front preceding a green color. The pieces remained in contact with solution for 17 hours at which point a visible separation was noted between the green and yellow color, and the yellow color had reached the top surface of the SCFS piece. The ambient samples remained in contact with the solution for an additional 3 hours. The samples continued to show clear separation of colors and the yellow color indicated a higher concentration of iodine at the top of the SCFS. The pieces were removed from their solutions and cut in half parallel to the long dimension, and the flow pattern the flow pattern was observed and measured. the flow pattern for all of the pieces exhibited a discrete green and yellow section, and each section showed penetration fronts parallel to the original liquid surface. Additionally, the topmost portion of the pieces showed a color saturation that indicated significant concentration enrichment of iodine across the width of the sample. This example demonstrated effect of solvent and temperature to affect rate of flow and showed continuous flow of the material through the substrate.

Example 4

Two samples of SCFS were machined into 33×9×9 mm pieces. One piece was place in a red solution of Oil Red O (Sigma Aldrich, St. Louis, Mo.) in benzene (0.1 mg/mL) and one piece was placed in a deep blue solution of Sudan Black B (Sigma Aldrich, St. Louis, Mo.) in benzene (0.1 mg/mL). The chemical formula for Oil Red O is $C_{26}H_{24}N_4O$ and the chemical formula for Sudan Black B is $C_{29}H_{24}N_6$ with the primary difference being two secondary amines on the Sudan Black B providing a higher degree of polarity, as well as a slightly larger molecular size. The SCFS pieces were placed in contact with the solution for 2.5 hours in accordance with Example 1 and the cut in half parallel the long dimension. The flow pattern was observed and measured. The sample that was penetrated with Oil Red O showed level filling similar to the four and five sided samples in Example 1. The piece that was penetrated with Sudan Black B showed similar flow pattern to Oil Red O except it showed a slight convex shape at the top of the dye penetration. This flow profile was created by the increased polarity of the solute/wall interaction under Nanoflow conditions. The penetration of Nanoflow for the Oil Red O and Sudan Black B were 20.3 mm and 10.7 mm with rates of 136 μm/min and 71.2 μm/min respectively. The significant increase in the Nanoflow rate of the non-polar system suggests strong solvent/wall interaction. This example demonstrated the effect of wall interaction on flow rate and pattern for both the solvent and solute.

Example 5

A solution was made by mixing 20 mg of Oil Red O and 20 mg of Sudan Black B in 50 mL of toluene resulting in a deep purple colored solution. Two samples of SCFS were machined into 30×9×9 mm pieces After approximately 10 minutes, the outer surfaces of the pieces showed separation of color with a red penetration front proceeding a purple front. The samples remained in contact with solution for 3.5 hours at which point a clear separation between the red and purple color of approximately 10 mm. The samples were polished on the four large rectangular sides approximately 1 mm to remove any potential edge flow effects. The sample cut in half parallel to the long dimension and the flow pattern exhibited two clear sections of a purple and a red color forming lines parallel to the original liquid surface expect the purple dye front showed a slight convex shape. The sample was then sectioned in half along the short dimension to isolate the red and the purple sections. These samples were then placed individual vial containing benzene and allowed to sit approximately 24 hours. The SCFS samples were removed from the vials. The vial containing the top portion was a clear red solution while the vial containing the bottom portion was a clear purple solution. This example demonstrated separation and extraction of solute using Nanoflow methods.

Example 6

A solution was made by mixing 0.5 mL of tin acetylacetonate (Sigma Aldrich, St. Louis, Mo.) and 50 mL of acetyl acetone (Sigma Aldrich, St. Louis, Mo.) resulting in an amber colored, clear solution. A sample of SCFS (30×9×9 mm) was placed in contact with the solution in accordance with Example 1. After a short period of time, the tin solution was seen to have been transported approximately 23 mm up the length of the outside surface of the SCFS sample. The sample was removed from the tin solution and heat treated in air at 250° C. for 4 hours, followed by 500° C. for 4 hours. The sample was allowed to cool, and helium pycnometry was then performed to evaluate density changes. The density of the SCFS remained unchanged from the tin solution exposure, yielding values of 2.26 g/cm². The SCFS sample was subsequently cut in half parallel to the long dimension. The two halves of the SCFS sample were analyzed in a scanning electron microscope for structural analysis and subjected to electron dispersive spectroscopy for material composition analysis. The SEM and EDS analysis showed that a layer of tin oxide was deposited in the internal regions of the SCFS, forming a coating layer that lines the walls of the internal porosity of the SCFS, while not filling the pores.

Example 7

A solution was made by adding 3 mL of acetyl acetone to 0.4 g of indium acetylacetonate (Sigma Aldrich, St. Louis, Mo.) and mixed. The clear saturation portion of the solution was extracted and used to deposit a layer of indium oxide along the internal pore walls of the SCFS in the same manner as described in Example 6. SEM and EDS characterization of the sample showed an indium oxide coating layer on the internal pore walls of the SCFS along with lack of filled pores.

Example 8

A sample of SCFS was machined into a 30×9×9 mm dimension piece and sealed on four sides with paraffin wax as described in Example 3. The piece was placed in a small glass cup such that one side the piece was in contact with the base of the cup with the 30 mm dimension perpendicular to the bottom of the cup. Approximately 2 mm of a solution containing *Enterobacteria phage* T4 virus (Carolina Biological Supply Company, Burlington, N.C.) in a water-nutrient solution was added to the cup such that the base of the SCFS piece was in contact with the solution. The cup was placed in an oven at 40° C. After 1 hour, water was observed to begin to flow from the top of the SCFS sample, having passed through the internal channel network of the SCFS. The SCFS piece was removed after 6 hours and the top part of the SCFS was cut off as a small piece and collected. A sample of the as-received solution was collected and added to a top agar culture of Escherichia Coil (Carolina Biological Supply Company, Burlington, N.C.) on an agar plate and incubated at 37° C. overnight, producing visible colonies of *E. Coli* infected with the T4 virus, which appear as circular regions with a translucent color on the agar plate, positively confirming the presence of the T4 virus. The T4 virus from the as-received solution was observed to infect over 99% of the *E. Coli* colonies (by surface area) during the overnight incubation. The top piece sample of the SCFS was similarly analyzed with the agar plate method using an overnight incubation period, with the results positively confirming the absence of over 95% the T4 virus (by surface area coverage of the translucent infected *E Coli* colonies), indicating that the T4 virus had been substantially removed from the water by filtration within the SCFS sample. A separate sample of SCFS was cut from an area in contact with the T4 virus laden solution after the 40° C. exposure was similarly analyzed with the agar plate method, with the results positively confirming the presence of the T4 virus (indicating that the oven did not kill the virus).

Example 9

Two 28 mm×11 mm silicon wafers (Lightsmyth Technologies Inc., Eugene, Oreg.) containing etched trenches on one side of the wafers were placed in a flat glass dish. The trenches were 140 nm width×110 nm depth×11 length in a regular pattern travelling perpendicular to the long side of the wafers. One of the wafers was treated with a vapor deposited silver coating on the surface, carefully applied to form a solid layer that covered the trenches, effectively creating a roof over the trenches, forming a parallel array of nanopipes. The wafers in the glass dish were placed standing on-edge, such that the long side of the wafers was in contact with the dish, and subsequently tilted to an angle such that the face of the wafers containing the nano-groove trenches is approximately 0.5 mm above the surface of the glass. A 1.0 Molar solution of aluminum nitrate dissolved in ethanol was added to the dish at room temperature until the meniscus of the liquid pool was in contact with the edge of the face of the wafers containing the nano-grooves (about 2 mL). The liquid was observed to wet both wafers on the contacting edge. After about five minutes, in the wafer containing the enclosed trenches, vapor was observed to flow out of the distal end of the enclosed trenches, at the top wafer edge. The vapor was seen to envelop the top edge of the wafer, and small quantities of liquid were observed at the top edge of the wafer soon thereafter, forming small droplets on the wafer edge that coalesced into a liquid meniscus that wetted a small portion of the face of the wafer near the top edge. For the open channel wafer, liquid remained at the bottom of the wafer in the form of a small meniscus. The samples were heated to dry the liquid solution. The samples were examined using scanning electron microscopy (SEM) and electron dispersive spectroscopy (EDS), and the nanopipe array sample showed that aluminum and oxygen containing material is present on the inside of the nanopipes throughout the length of the channels. The open groove sample was observed to have a lack of any material in the grooves. By using enclosure of nanochannels, Nanoflow is enabled in otherwise non-usable systems.

What is claimed is:

1. A method of transporting a liquid through a material containing nanochannels, the method comprising:
    contacting a surface of the material with the liquid, the liquid containing at least one solute and at least one vaporizable solvent, diameters of the nanochannels not exceeding about 300 nm, and the nanochannels being in open communication with the surface of the material; and
    maintaining contact of the liquid with the surface of the material under temperature and pressure conditions sufficient to cause a partial vaporization of the vaporizable solvent;
    wherein the maintaining step causes the partial vaporization of the vaporizable solvent within the nanochannels; and
    wherein said partial vaporization of the vaporizable solvent causes the liquid to be transported as annular flow along interior wall surfaces of the nanochannels.

2. The method of claim 1 in which the diameters of the nanochannels do not exceed about 100 nm.

3. The method of claim 1, wherein the vaporizable solvent is water, a C1-C10 alcohol, or a mixture thereof.

4. The method of claim 1 further comprising:
    drying the liquid along the interior wall surfaces of the nanochannels to remove the vaporizable solvent from the nanochannels and to form a first film layer of the solute on the interior wall surfaces.

5. The method of claim 4, wherein the first film layer has a thickness of less than 50 nm.

6. The method of claim 4 further comprising forming a second film layer on the first film layer.

7. The method of claim 4, wherein the solute is releasable from the material.

8. The method of claim 4, further comprising pyrolyzing the first film layer carried on the interior wall surfaces forming a pyrolyzed film layer.

9. The method of claim 8, further comprising
    forming a second film layer on the pyrolyzed film layer; and
    then pyrolyzing the second film layer.

10. The method of claim 6, wherein the first and the second film layers have different compositions.

11. The method of claim 1, wherein the partial vaporization of the vaporizable solvent provides a locally dynamic pressure gradient within the nanochannels.

12. The method of claim 1,
    wherein the vaporizable solvent consists of water, a C1-C10 alcohol, or a mixture thereof; and
    after transport of the liquid along the nanochannel interior wall surfaces, the method further comprises then removing the vaporizable solvent from the material thereby forming a first film layer of the solute on the interior wall surfaces.

13. The method of claim 11, wherein the locally dynamic pressure gradient is provided by heating the material to a temperature below a boiling point of the vaporizable solvent.

14. The method of claim 13, wherein the vaporizable solvent includes water and the material is heated to a temperature above about 50° C.

15. The method of claim 14, wherein the material is heated to a temperature of about 60° C.

16. The method of claim 12 further comprising forming a second film layer on the first film layer.

17. The method of claim 16 further comprising pyrolyzing the film layers.

18. The method of claim 12 further comprising pyrolyzing the first film layer.

19. The method of claim 1, further comprising:
after transport of the liquid along the nanochannel interior wall surfaces, altering the temperature or pressure conditions to enable pyrolysis and deposition of a solid film on the interior wall surfaces.

20. The method of claim 1, further comprising:
filtering out solid particles suspended in the liquid that are too large to flow through the nanochannels.

21. The method of claim 4, further comprising:
controlling a thickness of the first film layer, or of the first film layer plus one or more subsequently deposited additional film layers, to constrict a diameter of passageways in the nanochannels through which a liquid being filtered may be transported; and
transporting the liquid being filtered through the constricted passageways to filter out suspended solid particles that are too large to flow through the constricted passageways.

22. The method of claim 4, wherein the liquid comprises pharmaceuticals or biomolecules, and the first film layer consists of a known or calibrated volume of the pharmaceuticals or biomolecules, the method further comprising:
forming the material from a pharmaceutically acceptable substrate with precisely created vias that are covered to form the nanochannels with a known volume, geometry, or calibrated flow rate; and
after the drying step, transporting a delivery vaporizable liquid through the nanochannels to dissolve the first film layer and to deliver the pharmaceuticals or biomolecules at a precise rate or volume.

* * * * *